(12) United States Patent
Bristow

(10) Patent No.: US 9,072,298 B2
(45) Date of Patent: Jul. 7, 2015

(54) SYNERGISTIC HERBICIDAL COMPOSITION

(71) Applicant: ROTAM AGROCHEM INTERNATIONAL COMPANY LIMITED, Hong Kong (CN)

(72) Inventor: James Timothy Bristow, Hong Kong (CN)

(73) Assignee: ROTAM AGROCHEM INTRNATIONAL COMPANY LIMITED, Chai Wan, Hong Kong (CN)

(*) Notice: Subject to any disclaimer, the term of this patent is extended or adjusted under 35 U.S.C. 154(b) by 61 days.

(21) Appl. No.: 14/069,797

(22) Filed: Nov. 1, 2013

(65) Prior Publication Data
US 2015/0126369 A1 May 7, 2015

(51) Int. Cl.
*A01N 25/26* (2006.01)
*A01N 43/64* (2006.01)
*A01N 43/60* (2006.01)
*A01N 47/38* (2006.01)
*A01N 41/12* (2006.01)

(52) U.S. Cl.
CPC ............... *A01N 47/38* (2013.01); *A01N 41/12* (2013.01)

(58) Field of Classification Search
None
See application file for complete search history.

(56) References Cited

U.S. PATENT DOCUMENTS 5,013,659 A     5/1991    Bedbrook et al.

FOREIGN PATENT DOCUMENTS

| CN | 102405846 A | 4/2012 |
|---|---|---|
| EP | 0142924 A2 | 5/1985 |
| EP | 0257993 A2 | 3/1986 |
| EP | 0193259 A1 | 9/1986 |
| WO | 9113972 A1 | 9/1991 |
| WO | 9119806 A1 | 12/1991 |
| WO | 9211376 A1 | 7/1992 |
| WO | 9214827 A1 | 9/1992 |

OTHER PUBLICATIONS

S. R. Colby Calculating Synergistic and Antagonistic Responses of Herbicide Combinations, 2013.

*Primary Examiner* — Alton Pryor
(74) *Attorney, Agent, or Firm* — Dickinson Wright PLLC

(57) ABSTRACT

The present invention provides a synergistic herbicidal composition comprising a compound A and a compound B; wherein the compound A is one selected from the group consisting of clethodim and sethoxydim; wherein the compound B is one selected from the group consisting of thifensulfuron-methyl, tribenuron-methyl, cyclosulfamuron, bensulfuron-methyl, triasulfuron, mesosulfuron-methyl, monosulfuron, amidosulfuron, metsulfuron-methyl, chlorsulfuron and nicosulfuron; and the weight ratio between the compound A and the compound B is in the range from 100:1 to 1:100. The novel composition according to the present invention obtained by binary combining achieves a synergistic effect in controlling monocotyledonous weeds, dicotyledonous weeds and Cyperaceae weeds in the fields of resistant rapes and resistant soybeans.

10 Claims, No Drawings

SYNERGISTIC HERBICIDAL COMPOSITION

BACKGROUND OF THE INVENTION

1. Field

Disclosed herein is a synergistic herbicidal composition, particularly a synergistic herbicidal composition that can be applied in fields of resistant rapes, resistant soybeans and other crops.

2. Description of Related Art

Clethodim is also called Selectione or Seroxat. The chemical name thereof is: (±)-2-[(E)-3-chloroallyloxyimino]propyl-5-[2-(ethylthio)propyl]-3-hydroxycyclohexen-2-one, and the structure formula thereof is:

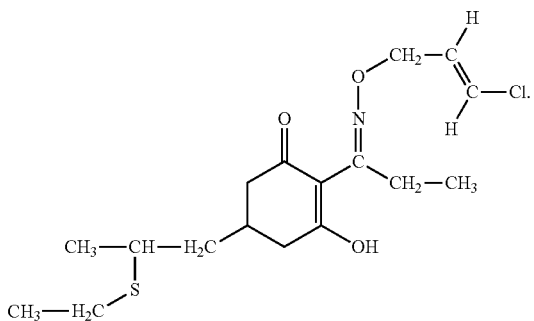 [SMILES: CCSC(C)CC1CC(=O)C(C(CC)=NOC/C=C/Cl)=C(O)C1]

Clethodim is a postemergence cyclohexenone herbicide for dry field with excellent selectivity. It is suitable for broadleaf fields such as soybean, rape, cotton, peanut, etc., to control Gramineae weeds, such as wild oat, *Digitaria, Setaria*, goosegrass, *Poa*, hard grass, etc. After application, it can be rapidly absorbed and transmitted to the shoot tip and meristem by the stems and leaves of Gramineae weeds, and inhibits the activity of the meristem, disrupts cell division, and eventually leads to the death of the weeds.

The chemical name of sethoxydim is (±)-2-[1-(ethoxyimino)butyl]-5-[2-(ethylthio)propyl]-3-hydroxy-2-cyclo hexen-1-one, and the structure formula thereof is:

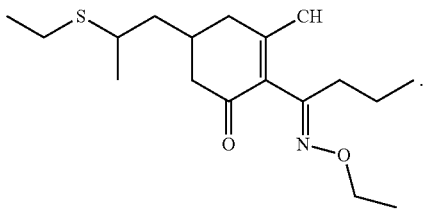 [SMILES: CCC/C(=N\OCC)C1=C(C)CC(CC(C)SCC)CC1=O]

Sethoxydim, which also belongs to the group of cyclohexenone herbicides, is a highly selective systemic conductive stem leaf processing agent, and can be rapidly absorbed by the stems and leaves of Gramineae weeds, and transmitted to the top and internode meristems, such that Gramineae weeds are killed by disrupting cell divisions. It can be used for crops such as soybean, cotton, rape, peanut, potato, beet, sunflower, flax, etc., and for orchards, to control barnyard grass, wild oat, *Setaria, Alopecurus, Digitaria*, goosegrass, etc., but it is ineffective with respect to broadleaf weeds.

The development of sulfonylurea herbicides began in the late 1970's. It has been reported by Levitt et al. in 1978 that preemergence soil treatment or postemergence foliar treatment with chlorsulfuron at a very low dosage can effectively control the majority of weeds in the fields of wheat and flax. This was followed by the development of metsulfuron-methyl, and a series of other sulfonylurea compounds, such as sulfometuron methyl, chlorimuron-ethyl, tribenuron-methyl, thifensulfuron-methyl, bensulfuron-methyl, etc. have been developed subsequently. The development of these herbicides has been very rapid and they have been used in the fields of various crops. Some of the sulfonylurea herbicides have become the main herbicides used in fields of certain crops. Moreover, new compounds of sulfonylurea herbicides continue to be developed and commercialized. Sulfonylurea herbicides generally can be thought of as consisting of three moieties, i.e., an aromatic group, a sulfonylurea bridge, and a heterocyclic ring. Small changes in the substituents of one or more moieties can cause significant changes in biological activity and selectivity. The more common sulfonylurea herbicide products include: thifensulfuron-methyl, having the chemical name of: 3-(4-methoxy-6-methyl-1,3,5-triazin-2-yl)-1-(2-methoxyformylthiophen-3-yl)-sulfonylurea; tribenuron-methyl, having the chemical name of: methyl 2-[N-(4-methoxy-6-methyl-1,3,5-triazin-2-yl)-N-methylcarbamoylaminosulfonyl]benzoate; cyclosulfamuron, having the chemical name of: 1-{[O-(cyclopropylcarbonyl)phenyl]sulfamoyl}-3(4,6-dimethoxy-2-pyridinyl)-urea; bensulfuron-methyl, having the chemical name of: methyl 2-[((4,6-dimethoxypyrimidin-2-yl)aminocarbonylamino]sulfonyl methyl)benzoate; triasulfuron, having the chemical name of: 1-[2-(2-chloroethoxy)phenylsulfonyl]-3-(4-methoxy-6-methyl-1,3,5-triazin-2-yl)urea; mesulfuron-methyl, having the chemical name of: methyl 2-[(4,6-dimethoxypyrimidin-2-ylcarbamoyl)sulfamoyl]-α-(methanesulfonamido)-p-toluate; monosulfuron, having the chemical name of: 2-(4-methylpyrimidinyl)benzenesulfonylurea; amidosulfuron, having the chemical name of: 1-(4,6-dimethoxypyrimidin-2-yl)-3-mesyl(methyl)sulfamoylurea; metsulfuron-methyl, having the chemical name of: methyl 2-[(4-methoxy-6-methyl-1,3,5-triazin-2-yl)ureidosulfonyl]benzoate; chlorsulfuron, having the chemical name of: 1-(2-chlorophenyl)sulfonyl]3-(4-methyl-6-methyl-1,3,5-triazin-2-yl)urea; nicosulfuron, having the chemical name of: 2-(4,6-dimethoxypyrimidin-2-ylcarbamoylsulfamoyl)-N,N-dimethylnicotinamide.

Even with the existence of these herbicides, there remains a need in the art to control all the weeds in the field at one time, to expand the limit of herbicidal spectra of clethodim and sethoxydim herbicides and sulfonylurea herbicides, and to improve the herbicidal speed of clethodim or sethoxydim and sulfonylurea herbicides against dicotyledonous and monocotyledonous weeds.

SUMMARY

In order to solve the above-mentioned technical problems, the present invention provides a synergistic herbicidal composition that combines clethodim and/or sethoxydim with one or more sulfonylurea herbicides, which has been surprisingly found to achieve a synergistic effect on weeds in the fields of resistant rape and resistant soybean crops and thus significantly reducing the number of compounds required to control the weeds, without causing unacceptable phytotoxicity on crops. More specifically, the novel synergistic herbicidal composition obtained by binary combining achieves a synergistic effect for controlling monocotyledonous weeds and dicotyledonous weeds in the fields of resistant rape, resistant soybean, and other crops, and is safe with respect to the succeeding crops.

The technical solutions of embodiments disclosed herein to solve the technical problems are:

A synergistic herbicidal composition comprises a compound A and a compound B; wherein the compound A is one selected from the group consisting of clethodim and sethoxydim; wherein the compound B is one selected from the group consisting of thifensulfuron-methyl, tribenuron-methyl, cyclosulfamuron, bensulfuron-methyl, triasulfuron, mesulfuron-methyl, monosulfuron, amidosulfuron, metsulfuron-methyl, chlorsulfuron, and nicosulfuron; and wherein the weight ratio between the compound A and the compound B is in the range from 100:1 to 1:100, preferably from 50:1 to 1:50, more preferably from 10:1 to 1:10.

Certain embodiments of combinations of the compound A and the compound B of the synergistic herbicidal composition disclosed herein can be:
(1) clethodim+thifensulfuron-methyl;
(2) clethodim+tribenuron-methyl;
(3) clethodim+cyclosulfamuron;
(4) clethodim+bensulfuron-methyl;
(5) clethodim+triasuifuron;
(6) clethodim+mesosulfuron-methyl;
(7) clethodim+monosulfuron;
(8) clethodim+amidosulfuron;
(9) clethodim+metsulfuron-methyl;
(10) clethodim+chlorsulfuron;
(11) clethodim+nicosulfuron;
(12) sethoxydim+thifensulfuron-methyl;
(13) sethoxydim+tribenuron-methyl;
(14) sethoxydim+cyclosulfamuron;
(15) sethoxydim+bensulfuron-methyl;
(16) sethoxydim+triasulfuron;
(17) sethoxydim+mesosulfuron-methyl;
(18) sethoxydim+monosulfuron;
(19) sethoxydim+amidosulfuron;
(20) sethoxydim+metsulfuron-methyl;
(21) sethoxydim+chlorsulfuron;
(22) sethoxydim+nicosulfuron.

The synergistic herbicidal composition can be formulated into any agriculturally acceptable formulations, such as wettable powders, emulsifiable concentrates, suspension concentrates, oil-based suspension concentrates, micro-capsules, micro-emulsions, oil-in-water emulsion, suspo-emulsions, water dispersible granules, a mixed formulation of microencapsulated suspension and suspension concentrate (ZC) and ultra-low volume liquids.

Thus, also disclosed herein is a synergistic herbicidal composition comprising a combination of an effective amount of the compound A and the compound B mixed with at least one additives commonly used in formulation techniques.

Also disclosed herein is a method for controlling undesired plants, comprising applying a synergistic herbicidal composition as disclosed herein to plants, plant tissues, plant seeds or cultivation areas during preemergence, or during postemergence, or during preemergence and postemergence. In a particular embodiment, the undesired plants are monocotyledonous weeds and dicotyledonous weeds.

In particular embodiments, the undesired plants can include various forms of *Stellaria, Nasturtium, Agrostis, Digitaria, Avena, Setaria, Sinapis, Lolium, Solanum, Bromus, Alopecurus, Matricaria, Abutilon, Sida, Xanthium, Amaranthus, Chenopodium, Ipomoea, Chrysanthemum, Galium, Viola* and *Veronica*.

Also disclosed herein is a method for controlling the growth of undesired plants in sulfonylurea-resistant rape and soybean crops comprising applying at least one of the compound A and at least one of the compound B to undesired plants, plant tissues thereof or cultivation areas.

Also disclosed herein is a herbicidal composition of a compound A and a compound B, and a herbicide composition comprising them.

DETAILED DESCRIPTION OF SPECIFIC EMBODIMENTS

Preparing a pesticide from various combinations of compounds of pesticides can be an effective and efficient method for the development and research of novel pesticides, such as those for controlling agricultural weeds. The combining of different varieties of pesticide can generally exhibit one of three types of effects with respect to a particular weed: an additive effect, a synergistic effect, or an antagonistic effect. The particular effect that a pesticide combination will exhibit is unpredictable, and can only be determined by conducting a large number of experiments. As used herein, the terms "herbicidal compound" and "herbicidal substance" are used interchangeably to refer to an active chemical species having the desired herbicidal activity and included in the composition for this purpose.

Synergistic combinations of herbicidal compounds or substances are particularly desirable because they significantly increase the effect of the actual control of the weeds, and thus reduce the necessary dosage of the individual herbicidally active compounds or substances. This reduction in dosage greatly slows down the rate at which weeds acquire herbicide resistance, thus it is-an important and very desirable means for effectively controlling weeds.

A particularly desirable synergistic herbicidal composition is a combination of at least two herbicidally active compounds or substances as disclosed herein. These compositions comprise a compound A and a compound B, wherein the compound A is one selected from the group consisting of clethodim and sethoxydim; wherein the compound B is one selected from the group consisting of thifensulfuron-methyl, tribenuron-methyl, cyclosulfamuron, bensulfuron-methyl, triasulfuron, mesosulfuron-methyl, monosulfuron, amidosulfuron, metsulfuron-methyl, chlorsulfuron, and nicosulfuron; and wherein the weight ratio between the compound A and the compound B is in the range from 100:1 to 1:100, preferably from 50:1 to 1:50, and more preferably from 10:1 to 1:10.

Combinations of the compound A and the compound B of the synergistic herbicidal compositions according to the present invention can be:
(1) clethodim+thifensulfuron-methyl;
(2) clethodim+tribenuron-methyl;
(3) clethodim+cyclosulfamuron;
(4) clethodim+bensulfuron-methyl;
(5) clethodim+triasulfuron;
(6) clethodim+mesosulfuron-methyl;
(7) clethodim+monosulfuron;
(8) clethodim+amidosulfuron;
(9) clethodim+metsulfuron-methyl;
(10) clethodim+chlorsulfuron;
(11) clethodim+nicosulfuron;
(12) sethoxydim+thifensulfuron-methyl;
(13) sethoxydim+tribenuron-methyl;
(14) sethoxydim+cyclosulfamuron;
(15) sethoxydim+bensulfuron-methyl;
(16) sethoxydim+triasulfuron;
(17) sethoxydim+mesosulfuron-methyl;
(18) sethoxydim+monosulfuron;
(19) sethoxydim+amidosulfuron;

(20) sethoxydim+metsulfuron-methyl;
(21) sethoxydim+chlorsulfuron; and
(22) sethoxydim+nicosulfuron.

The specific combinations of the compound A and compound B disclosed herein are synergistic because they exceed the expected additive effect in principle on the weeds to be controlled, and thus widen the activity spectrum of two compounds, particularly in the following two aspects: firstly, the application rate of the individual compounds in the composition are reduced while a good level of action is maintained; and secondly, the synergistic herbicidal compositions achieve a high level of weed control even in the case of a low rate of application of the individual herbicidal substance, including rates that are so low as to be considered ineffective in the view of agriculture industry. The result is that the activity spectrum of weeds is considerably wider and additionally that the selectivity to useful plant crops is increased. This satisfies a necessity and desire to avoid unintentional overdosing of individual herbicidal compounds. The synergistic herbicidal composition disclosed herein maintains excellent control of weeds among useful plants, and also allows greater adaptability for the succeeding crops.

The synergistic herbicidal composition can also contain combinations of an effective amount of a compound A and a compound B mixed with at least one additive which is normally used in formulation technology, including, but not limited to, those described in more detail below.

The additives used in the synergistic herbicidal composition of the present invention include those that comprise liquid carriers, solid carriers, dispersing agents, emulsifiers, stabilizers, anti-freezing agent, thickeners, etc., and other well known substances which are useful for stabilizing the compounds (i.e. active ingredients) and exerting efficacy in the formulation, all of which are various substances commonly used or allowed to be used in pesticides, without particular limitation, and particular ingredients and dosages are determined by simple tests according to the formulation requirements.

The liquid carriers suitable for preparing the synergistic herbicidal composition of the present invention include those that comprise aromatic hydrocarbons and/or aliphatic hydrocarbons. Polar solvents, such as alcohols and ethers and esters thereof can also be used, and are particularly applicable. In addition, vegetable oils and soluble methyl cellulose are also suitable. Meanwhile, a mixture of different liquids, including mixtures of the above liquids, is also applicable.

The solid carriers suitable for the synergistic herbicidal composition of the present invention include those containing diatomite, aluminum magnesium silicate, activated clay, kaolin, clay, gypsum, bentonite, white carbon black, light calcium carbonate, lime stone, saw dust, corn starch, soluble starch, etc., and mixtures thereof.

The emulsifiers suitable for preparing the synergistic herbicidal composition of the present invention can include anionic and/or nonionic emulsifiers, such as alkylphenol polyoxyethylene ether, alkylphenol polyoxyethylene polyoxypropylene ether, benzylphenol polyoxyethylene ether, polyoxyethylene fatty acid ester, polyoxyethylene fatty alcohol ether, polyoxyethylene fatty amine, alkylphenol polyglycol ether, etc., and mixtures thereof.

The dispersing agents suitable for preparing the synergistic herbicidal composition of the present invention can include alkyl naphthalenesulfonate, bis(alkyl)naphthalenesulfonate formaldehyde condensate, naphthalenesulfonate formaldehyde condensates, alkylphenol polyoxyethylene phosphate, alkylphenol polyoxyethylene ether formaldehyde condensate sulfate, alkylphenol polyoxyethylene ether phosphate, alkylphenol polyoxyethylene ether, castor oil ethylene oxide adduct, ethylene oxide-propylene oxide block copolymers, alkylphenol polyoxyethylene ether formaldehyde condensates, octylphenol polyoxyethylene ether sulfate and methyl cellulose. For example, sodium lignosulfonate, calcium lignosulfonate, sodium methyl naphthalenesulfonate formaldehyde condensate, sodium naphthalenesulfonate formaldehyde condensate, sodium methylene naphthalenesulfonate, etc., and mixtures thereof, are particularly suitable.

Examples of other additives include carboxymethyl cellulose, ethylene glycol, propylene glycol, etc., which are commonly used as auxiliaries in herbicidal formulations, and can provide stabilizing, thickening, and anti-freezing effects.

The synergistic herbicidal composition of the present invention can also contain colorant, for example, inorganic pigments such as iron oxide, titanium oxide or Prussian blue, etc.; organic dye such as Alizarin, azo dyes, metal phthalocyanine blue or triphenylmethane dyes, etc.

The composition of the present invention can be used in any commonly used formulations, including those indicated by the abbreviations below.

GR: granules
WP: wettable powders
WG: water dispersible granules
SG: soluble granules
SL: soluble liquids
EC: emulsifiable concentrates
EW: oil-in-water emulsion
ME: microemulsion
SC: suspension concentrates
CS: microencapsulated suspensions
OD: oil-based suspension concentrates
SE: suspoemulsions Preferred formulations of the present invention include wettable powders, emulsifiable concentrates, suspension concentrates, oil-based suspension concentrates, micro-capsules, micro-emulsions, oil-in-water emulsion, suspo-emulsions, water dispersible granules, a mixed formulation of microencapsulated suspension and suspension concentrate (ZC), and ultra-low volume liquids.

For water dispersible granules, the person skilled in the art is familiar with using appropriate auxiliaries to obtain a desired granule containing a synergistic composition disclosed herein. A dispersing agent, which may be selected from the group consisting of polycarboxylate, lignosulfonate, alkyl naphthalenesulphonate, alkylphenol polyoxyethylene ether, EO/PO block polyether, and mixtures thereof; a wetting agent, which may be selected from the group consisting of alkyl sulfates, alkyl sulfonate, naphthalenesulfonate, sodium lignosulfonate, fatty alcohol polyoxyethylene ether, alkylphenol polyoxyethylene ether, and mixtures thereof; a disintegrant, which may be selected from the group consisting of ammonium sulfate, sodium sulfate, sodium chloride, ammonium chloride, urea, sucrose, glucose, carboxymethyl cellulose, soluble starch, polyvinylpyrrolidone, and mixtures thereof; a binder, which may be selected from the group consisting of polyvinyl alcohol, soluble starch, dextrin, xanthan gum, carboxymethyl(ethyl) cellulose, and mixtures thereof; and a filler, which may be selected from the group consisting of diatomite, kaolin, white carbon black, light calcium carbonate, talc, attapulgite, pottery clay, and mixtures thereof.

For wettable powders, the auxiliaries which can desirably be used are: a dispersing agent, which may be selected from the group consisting of polycarboxylate, lignosulfonates, alkyl naphthalenesulfonate, and mixtures thereof; a wetting agent, which may be selected from the group consisting of alkyl sulfate, alkyl sulfonate, naphthalenesulfonate, and mixtures thereof; a filler, which may be selected from the group consisting of ammonium sulfate, urea, sucrose, glucose, diatomite, kaolin, white carbon black, light calcium carbonate, talc, attapulgite, pottery clay, and mixtures thereof.

For suspension concentrates, the auxiliaries which can desirably be used are: a dispersing agent, which may be selected from the group consisting of polycarboxylate, lignosulfonates, alkyl naphthalenesulfonate, TERSPERSE® 2425 (manufactured by Huntsman Corporation, U.S., alkyl naphthalenesulfonates), and mixtures thereof; an emulsifier, which may be selected from the group consisting of Pesticide Emulsifier 700# (generic name: alkylphenol formaldehyde resin polyoxyethylene ether), Pesticide Emulsifier 2201, SPAN® 60 (generic name: sorbitan monostearate), Emulsifier TWEEN® 60 (generic name: polyoxyethylene sorbitan monostearate), Pesticide Emulsifier 1601 # (generic name: phenylethylphenol polyoxyethylene polyoxypropylene ether), TERSPERSE® 4894 (manufactured by Huntsman Corporation, U.S.), and mixtures thereof; a wetting agent, which may be selected from the group consisting of alkylphenol polyoxyethylene ether formaldehyde condensate sulfate, alkylphenol polyoxyethylene ether phosphate, phenylphenol polyoxyethylene ether phosphates, alkyl sulfates, alkyl sulfonates, naphthalenesulfonate, TERSPERSE® 2500 (manufactured by Huntsman Corporation, U.S.), and mixtures thereof; a thickener, which may be selected from the group consisting of xanthan gum, polyvinyl alcohol, bentonite, aluminum magnesium silicate, and mixtures thereof; a preservative, which may be selected from the group consisting of formaldehyde, benzoic acid, sodium benzoate, and mixtures thereof; an antifoaming agent, which may be an organic silicon antifoaming agent; and an anti-freezing agent, which may be selected from the group consisting of ethylene glycol, propylene glycol, glycerol, urea, inorganic salts (such as sodium chloride), and mixtures thereof.

For oil-based suspension concentrates, the auxiliaries which can desirably be used are: a dispersing agent, which may be selected from the group consisting of polycarboxylate, lignosulfonate, alkyl naphthalenesulfonate (Dispersant NNO), TERSPERSE® 2425, and mixtures thereof; an emulsifier, which may be selected from the group consisting of emulsifier BY (castor oil polyoxyethylene ether) series (BY-110, BY-125, BY-140), Pesticide Emulsifier 700# (generic name: alkylphenol formaldehyde resin polyoxyethylene ether), Pesticide Emulsifier 2201, SPAN® 60 (generic name: sorbitan monostearate), TWEEN® 60 (generic name: polyethylene glycol sorbitan monostearate), Pesticide Emulsifier 1601# (generic name: phenethylphenol polyoxyethylene polyoxypropylene ether), TERSPERSE® 4894, and mixtures thereof; a wetting agent, which may be selected from the group consisting of alkylphenol polyoxyethylene ether formaldehyde condensate sulfates, alkylphenol polyoxyethylene ether phosphate, phenylethylphenol polyoxyethylene ether phosphate, alkyl sulfate, alkyl sulfonate, naphthalenesulfonate, TERSPERSE® 2500, and mixtures thereof; a thickener, which may be selected from the group consisting of white carbon black, polyvinyl alcohol, bentonite, aluminum magnesium silicate, and mixtures thereof; an anti-freezing agent, which may be selected from the group consisting of ethylene glycol, propylene glycol, glycerol, urea, inorganic salts (such as sodium chloride), and mixtures thereof; a stabilizer, which may be selected from the group consisting of epoxidized soybean oil, epichlorohydrin, triphenyl phosphate, and mixtures thereof; a dispersion medium, which may be selected from the group consisting of soybean oil, rapeseed oil, corn oil, methyl oleate, diesel oil, machine oil, mineral oil, and mixtures thereof.

Examples of formulations suitable for compositions for tank mixing include solutions, diluted emulsions, suspension concentrates, or a mixture thereof, and powders.

Generally, the compositions for tank mixing are one or more premix composition comprising different active herbicidal compounds or substances and optionally additional auxiliaries, produced by diluting with solvent (e.g. water).

Typically, a foliar tank mix formulation comprises 0.1-20 wt %, particularly 0.1-15 wt %, of the active herbicidal compounds or substances, and 99.9-80 wt %, particularly 99.9-85 wt %, solid and/or liquid auxiliaries (comprising solvent such as water), wherein the auxiliaries can include a surfactant with a content of 0-20 wt %, particularly 0.1-15 wt %, based on the weight of the tank mix formulation.

Generally, premix formulations applied to foliage comprise 0.1-99 wt %, particularly 1-95 wt %, of the active herbicidal compounds, and 99.9-0.1 wt %, particularly 99-5 wt %, solid and/or liquid auxiliaries (comprising, e.g., solvent such as water), wherein the auxiliaries can be a surfactant with a content of 0-50 wt %, particularly 0.5-40 wt %, based on the weight of the premix formulation.

The formulated compositions described comprise 0.5-99.9 wt %, particularly 1-95 wt %, advantageously 1-50 wt %, of the active herbicidal compounds, and 99.5-0.1 wt %, particularly 99-5 wt %, solid and/or liquid adjuvants (comprising e.g. solvent such as water), wherein the auxiliaries (or adjuvants) can be a surfactant with 0-50 wt %, particularly 0.5-40 wt %, based on the weight of the premix formulation.

Depending upon the features of the formulation, application methods can be selected in accordance with intended subjects and prevailing environment, and can include techniques such as foliar feeding, soaking, spraying, dusting, and scattering.

When applied, the formulation can be in commodity form, i.e., undiluted. If necessary, the formulation (for example, wettable powders, emulsifiable concentrates, dispersible concentrates, and water dispersible granules), can be diluted with water in a conventional manner. For formulations of powders, granules for soil application, granules for dusting, and solution for spraying are generally not diluted with other inert substances before use.

The composition can be applied to plants, plant tissues, plants seeds or cultivation areas (ploughed), and is preferably applied to green plants and plant tissues. If necessary, the composition can also be applied to the ploughed soil.

It is also possible to apply the compositions disclosed herein as tank-mix formulations, wherein each substance is in a concentrated optimal formulation and is mixed with water in the tank and the obtained spray mixture is applied.

The advantage of the herbicidal composition obtained by pre-mixing the compound A and the compound B as disclosed herein is that the composition can be applied more conveniently because dosages of the compounds have been adjusted to an appropriate proportion. Moreover, this manner of application is a good way to select one or more suitable auxiliaries. Moreover, tank-mixing of various formulations may lead to unnecessary or undesired auxiliaries, which are present in the individual formulations, being mixed therewith.

Also disclosed herein is a method for controlling the growth of undesired plants, comprising applying the synergistic herbicidal composition to plants, plant tissues, plants seeds, or cultivation areas during preemergence, or during postemergence, or during preemergence and postemergence.

The undesired plants are monocotyledonous weeds and dicotyledonous weeds. Illustrative examples of undesired plants include *Stellaria, Nasturtium, Agrostis, Digitaria, Avena, Setaria, Sinapis, Solanum, Bromus, Alopecurus, Matricaria. Abutilon, Sida, Xanthium, Amaranthus, Chenopodium, Ipomoea, Chrysanthemum, Galium, Viola* and *Veronica*.

The cultivation areas suitable for application of the compositions disclosed herein are areas of land or fields in which the cultivated plants have been growing or the seeds of those cultivated plants have been sown, as well as areas of land in which the cultivated plants are intended to be cultivated.

The effective amount of the synergistic composition disclosed herein to be applied to plants, plant tissues, plant seeds, or cultivation areas may vary depending on the prevailing conditions at the time and place of application, such as weed pressure, time of application, manner of application, weather, soil condition, terrain features, species of target crop, etc. During application, a generally suitable application rate is about 0.001 kg/ha-1.00 kg/ha, preferably about 0.01 kg/ha-0.075 kg/ha of the composition. The effective amount of the synergistic composition disclosed herein may also vary depending on variables such as the concentration of active compound in the formulation, the type of formulation, particular combination of the compound (A) and the compound (B), the weight ratio of the compound (A) to the compound (B) in the formulation. The application rate for a particular set of conditions can be determined by conducting routine experimentation.

The method disclosed herein is used most preferably for controlling weeds in regions where crops are currently growing, or in regions where crops will be planted. When the composition is used in regions where crops are currently growing regions, the application rate of the composition should be enough to control the growth of the weeds, but not so great as to produce serious permanent damage to the crops. This application rate can be determined by experimentation using the particular combination of composition, crop, and weed.

The synergistic herbicidal composition disclosed herein can be applied during preemergence, postemergence, as well as both preemergence and postemergence. The preferable mode of application is postemergence, especially at the early growth period of weeds. Applying the herbicidal composition before planting (particularly applying on soil surface) is also one of the modes of application of the method disclosed herein.

The preemergence application of the synergistic herbicidal composition disclosed herein typically takes place on the soil surface. The synergistic herbicidal composition applied in this way can either completely prevent weeds from emerging, or make the weed seedlings at true leaf stage stop growing and then completely die after 3 to 4 weeks.

The postemergence application of the synergistic herbicidal composition disclosed herein typically takes place on the green parts of the plants, which stop growing soon after applying the composition. The weed plants remain at the growth stage when the composition is applied, or die rapidly after a period of time, so that the effect of the weeds, which are competitive with the crops, can be eliminated or permanently reduced by treating them as soon as possible with the disclosed synergistic herbicidal composition. Therefore, this method can rapidly and permanently reduce competition from weeds, which are harmful to crops.

The synergistic herbicidal composition disclosed herein has more rapid and more permanent herbicidal effects compared with single agent. It's particularly advantageous that, because of the synergism between compound A and compound B, the effective dose of the compound A and the compound B of the composition can be adjusted to a low level, so as to achieve their best effect in soil. As a result, not only can these compounds be applied to sensitive crops, but also the low levels of application can result in substantially avoiding contaminating ground water as a result of application of the compounds. Thus, by using the synergistic herbicidal composition of the present invention, the amount of compounds applied can be significantly reduced, the spectrum of crops that can be treated can be significantly increased, and adverse environmental effects can be significantly reduced.

In a particular embodiment, the synergistic herbicidal composition disclosed herein has excellent herbicidal activities against monocotyledonous and dicotyledonous weeds, while doing very little harm or no harm to resistant rape and/or resistant soybean. The composition and method disclosed herein are therefore especially suitable for application to resistant rape and resistant soybean using the application methods described above.

Resistant rape and resistant soybean comprise:

genetically recombined and modified crops with the purpose of improving the synthesis of the starch in plants; (for example, WO92/11376, WO92/14827, and WO91/19806);

genetically modified crops resistant to other herbicides such as sulfonylurea herbicides (EP0257993A, U.S. Pat. No. 5,013,659A);

non genetically modified crops resistant to other herbicides such as sulfonylurea herbicides (CN102405846A);

genetically modified crops which can produce thuricin of *Bacillus thuringiensis* (Bt toxins), so as to make the plants resistant to certain pests (EP0142924 A, EP0193259A);

genetically modified crops with improved fatty acid composition (WO91/13972).

In principle, the resistant plant can be any variety of the desired plant, i.e., it can be monocotyledonous and dicotyledonous plants.

Therefore, disclosed herein is also a method for controlling the growth of undesired plants among resistant rape and resistant soybean, comprising applying at least one of a compound A and at least one of a compound B to undesired plants, plant tissues thereof, or cultivation areas.

Also described herein is a synergistic herbicidal composition of a compound A and a compound B, and a herbicide composition comprising them.

The following examples are provided to further illustrate various features of the compositions described herein, and to provide guidance to those of skill in the art in making the compositions.

FORMULATION EXAMPLES

Example 1

Oil-Based Suspension Concentrates

Sethoxydim 25%
Metsulfuron-methyl 1%
Methyl naphthalenesulfonate formaldehyde condensate 10%
Bentonite 1%
Glycerol 5%
Corn oil make up to 100%

The components of metsulfuron-methyl, dispersing agents, wetting agents, and corn oil, etc. were mixed homogeneously according to the proportions in the formulation given above, ground and/or highly sheared to give an oil-based suspension concentrate of metsulfuron-methyl. Then sethoxydim was added and was stirred homogeneously with high-speed.

Example 2

Wettable Powders

Sethoxydim 2%
Nicosulfuron 10%
Sodium dodecyl sulfate 10%
Sodium lignosulfonate 5%
White carbon black 10%
Kaolin make up to 100%

The compounds, various auxiliaries and fillers, etc. were mixed according to the proportions of the formulation given above, and ground by ultrafine grinding mill to obtain wettable powders.

Example 3

Wettable Powders

Sethoxydim 1%
Tribenuron-methyl 50%
Calcium dodecyl benzenesulfonate 1%
Sodium lignosulfonate 2%
White carbon black make up to 100%

Sethoxydim, tribenuron-methyl, various auxiliaries, and fillers, etc. were mixed according to the proportions of the formulation given above, and ground by ultrafine grinding mill to obtain the wettable powders.

Example 4

Water Dispersible Granule

Sethoxydim 0.1%
Thifensulfuron-methyl 1%
Sodium lignosulfonate 4%
Sodium dodecyl sulfate 5%
Urea 5%
Kaolin make up to 100%

Sethoxydim, Thifensulfuron-methyl, dispersing agents, wetting agents, disintegrants and fillers were mixed homogeneously according to the proportion of the formulation, broken into wettable powders by jet milling. Wettable powders were added with an amount of water sufficient to provide an extrudable paste, mixed, granulated by extrusion and then dried and sieved to obtain water dispersible granules.

Example 5

Emulsifiable Concentrates

Sethoxydim 5%
Bensulfuron-methyl 0.1%
Ethoxylated castor oil 5%
Calcium dodecyl benzenesulfonate 3%
Dimethyl sulfoxide make up to 100%

The above ingredients were formulated according to the proportions given above by mixing homogeneously to obtain a homogeneous phase.

Example 6

Oil-Based Suspension Concentrates

Sethoxydim 10%
Chlorsulfuron 0.1%
Sodium methyl naphthalenesulfonate-formaldehyde condensate 5%
Ethoxylated castor oil 3%
Bentonite 1%
Aromatic hydrocarbon solvent 100 20%
Water make up to 100%

Chlorsulfuron, sodium methyl naphthalenesulfonate formaldehyde condensate were ground and/or high speed sheared to obtain a suspension concentrate of chlorsulfuron; sethoxydim, aromatic hydrocarbon solvent 100, ethoxylated castor oil were mixed and stirred homogeneously to obtain the an emulsifiable concentrate of sethoxydim; the resulting chlorsulfuron was added to the emulsifiable concentrate of sethoxydim to obtain oil-based suspension concentrates.

Example 7

Wettable Powders

Clethodim 1%
Monosulfuron 20%
Sodium dodecyl sulfate 10%
Sodium lignosulfonate 5%
White carbon white 10%
Kaolin make up to 100%

The above components were mixed according to the proportions given above, ground and crushed to prepare wettable powders.

Example 8

Water Dispersible Granules

Clethodim 4%
Amidosulfuron 4%
Modified calcium lignosulphonate 5%
Sodium dodecyl sulfate 5%
Urea 5%
Kaolin make up to 100%

Amidosulfuron, dispersing agent, wetting agent, disintegrant and filler were mixed homogeneously according to the proportions of the formulation given above and crushed by jet milling to obtain wettable powders. The wettable powders were added with clethodim and mixed homogeneously, and then were added with an amount of water sufficient to provide an extrudable paste, mixed, granulated by extrusion, and then dried and sieved to obtain water dispersible granules.

Example 9

Suspo-Emulsions

Oil Phase:
Clethodim 2%
Methyl oleate 10%
Ethoxylated castor oil 5%

Aqueous Phase:
Chlorsulfuron 50%
Modified calcium lignosulphonate 1%
Water make up to 100%

Clethodim was dissolved in methyl oleate. Ethoxylated castor oil was added to methyl oleate to obtain the oil phase. Chlorsulfuron, modified calcium lignosulphonate and water were sand milled according to the formulation to obtain suspension aqueous phase of chlorsulfuron. The oil phase was added to the aqueous phase with stirring to obtain suspo-emulsions.

Example 10

Wettable Powders

Clethodim 5%
Metsulfuron-methyl 10%
Sodium lignosulfonate 1%
Sodium dodecyl sulfate 2%
Highly dispersed silicic acid 1%
Kaolin make up to 100%

The above components were mixed according to the proportions given above, and then ground and crushed to prepare wettable powders.

Example 11

Coated Granules

Clethodim 1%
Nicosulfuron 25%
Polyethylene glycol 3%
Highly dispersed silicic acid 1%
Calcium carbonate make up to 100%

In a mixer, the finely ground clethodim and nicosulfuron were coated homogeneously onto the carrier wetted with polyethylene glycol. The dustless coated granules can be obtained in this way.

Example 12

Wettable Powders

Clethodim 1%
Mesosulfuron-methyl 5%
Sodium dodecyl sulfate 1%
Sodium lignosulfonate 1%
Kaolin make up to 100%

The above ingredients were mixed according to the proportions given above, and ground and crushed to prepare wettable powders.

Example 13

Extruded Granules

Clethodim 20%
Triasulfuron 10%
Sodium lignosulfonate 4%
Carboxymethyl cellulose 2%
Kaolin make up to 100%

Clethodim and triasulfuron were mixed with auxiliaries and ground to form a mixture. The mixture was wetted with water. The mixture was extruded and then dried under airflow.

Example 14

A Mixed Formulation of Microencapsulated Suspension and Suspension Concentrate (ZC)

ATLOX™ 4913 4%
Citric acid 0.05%
Catalyst 0.1%
Water 13%
Bensulfuron-methyl 10%
PAPI™ 1.35%
SOLVESSO™ 200 10%
ATLOX™ 4913 16%
Dispersing agent LFH 0.3%
Antifoaming agent 0.16%
Urea 8.4%
Clethodim 0.1%
Water make up to 100%

The oil phase formed by PAPI™, clethodim, and SOLVESSO™ 200 was added into an aqueous solution containing ATLOX™ 4913 to form an emulsion. The emulsion was then heated and kept at 50° C. The catalyst was added to the emulsion and reacted for 2 hours. Microencapsulated suspension of clethodim was obtained after cooling.

ATLOX™ 4913, dispersing agent LFH, antifoaming agent, urea, bensulfuron-methyl and water were mixed homogeneously according to the proportion, and sand milled to prepare a suspension concentrate.

The microencapsulated suspension of clethodim was added into the suspension concentrate of bensulfuron-methyl, and stirred homogeneously to obtain ZC.

Example 16

Suspo-Emulsions

Clethodim 10%
Cyclosulfamuron 12%
SOLVESSO™ 200 10%
Ethoxylated castor oil 4%
Fatty alcohol polyoxyethylene ether
sulfosuccinate monoester disodium 5%
Modified calcium lignosulphonate 5%
Xanthan gum 1%
Bentonite 1%
Glycerol 5%
Water make up to 100%

Clethodim was dissolved in SOLVESSO™ 200. Ethoxylated castor oil was added to the SOLVESSO™ 200 to obtain an emulsifiable concentrate of clethodim, i.e., an oil phase.

Cyclosulfamuron, fatty alcohol polyoxyethylene ether sulfosuccinate monoester disodium and modified calcium lignosulphonate were mixed homogeneously according to the proportion and sand milled. Ethoxylated castor oil, xanthan gum, bentonite and glycerol were added to prepare a suspension concentrate.

The oil phase of clethodim was added into the suspension concentrate containing cyclosulfamuron to obtain a suspo-emulsion.

Example 17

Emulsifiable Concentrate

Clethodim 10%
Tribenuron-methyl 2%
Ethoxylated castor oil 5%

Calcium dodecyl benzenesulfonate 3%
SOLVESSO™ 100 make up to 100%
The above various components were mixed and stirred to obtain a transparent and homogeneous phase.

Example 18

50% Compound A+50% Compound B

Clethodim 50%
Thifensulfuron-methyl 50%
Clethodim and thifensulfuron-methyl were mixed homogeneously according to the proportions given above.

Biological Test Example

A synergistic effect exists when the effect of the composition exceeds the sum of the effects of the compounds applied separately. The expected effect for a specific combination of two active compounds can be calculated using a so-called "Colby formula" (see S. R. Colby, "Calculating Synergistic and Antagonistic Responses of Herbicide Combinations", Weeds 1967, 15, 20-22) as follows: if X is the activity of the compound A when the application amount is in mg/ha or the concentration is in mppm;

Y is the activity of the compound B when the amount is in ng/ha or the concentration is in nppm, and is expressed by a percentage as compared to the untreated control;

E is the activity of the compounds A and B when the amount is in mg/ha and ng/ha or the concentration is in mppm and nppm, then $$E = X + Y - \frac{X \cdot Y}{100}$$

If the actually observed activity (O) is greater than the expected activity (E), then the composition is superadditive, i.e., synergism is present.

Through a large number of screening tests and effect analyses for different combinations and different ratios of the compounds A and B according to the present invention, the inventors have found that the obtained herbicidal composition have a particularly desirable synergistic effect, rather than only a simple addition of the two compounds, when the ratio of the compounds A and B is within certain range. Desirably, this range is in the range from 100:1 to 1:100, more particularly, from 50:1 to 1:50, even more particularly, from 10:1 to 1:10.

1. Preemergence Weed Control

The seeds or rhizomes of monocotyledoneous and dicotyledoneous undesired plants were placed into cardboard pots containing sandy loam and covered with soil. Embodiments of the compositions in forms of concentrated aqueous solution, wettable powder, or emulsifiable concentrate, were applied in various doses onto the surface of a soil cover layer. After treatment, the pot was positioned in greenhouse and the weeds were kept under excellent growth conditions. The test plants emerged after 3-4 weeks of the test. After the test plants emerged, the test plants were compared with the untreated control. Plant injury conditions or the adverse effects on the emergence were macroscopically observed and recorded. As shown in the test results, the compositions of the present invention applied during preemergence have a good herbicidal activity for a broad spectrum of monocotyledoneous and dicotyledoneous weeds.

2. Postemergence Herbicidal Effect

The seeds or rhizomes of monocotyledoneous and dicotyledoneous undesired plants were placed into cardboard pots containing sandy loam, covered with soil and cultivated under excellent growth conditions in a greenhouse. 3 weeks after sowing, the test plants were treated with embodiments of synergistic herbicidal compositions disclosed herein in trefoil stage. After the test plants were kept under the optimal growth conditions in the greenhouse for 3-4 weeks, the test plants were compared with the untreated control. The activity of the formulation was macroscopically observed and recorded. The compositions of the present invention applied during postemergence also have a very good herbicidal activity for a broad spectrum of economically important Gramineae weeds and broadleaf weeds.

It can be observed frequently that the activity of the composition of the present invention exceeds the sum of the activities of herbicides applied separately. The results show that the activity of the composition under appropriate low doses exceeds the expected value calculated according to the Colby formula.

3. Herbicidal Activity and Crop Tolerance (Field Test)

Sulfonylurea herbicides-resistant non-genetically modified rape crops were planted with typical weeds under natural outdoors conditions. When the rape plants grew, the weed populations naturally occurred. The weeds were treated during postemergence at 2-4 leaf stage. To reflect the synergistic effect, they were treated with a lower dosage than the common dosage. The result of the experiments are shown in Tables 1-7.

TABLE 1

Herbicidal activity against *Datura* four weeks after the treatment

| Treatment Application rate in gram ai/ha | Dosage | Injury of *Datura* % Experimental value | Predicted value |
|---|---|---|---|
| clethodim | 50 | 0 | — |
| thifensulfuron-methyl | 5 | 22 | — |
| tribenuron-methyl | 5 | 17 | — |
| cyclosulfamuron | 5 | 26 | — |
| bensulfuron-methyl | 5 | 32 | — |
| triasulfuron | 5 | 28 | — |
| mesosulfuron-methyl | 5 | 5 | — |
| monosulfuron | 5 | 24 | — |
| amidosulfuron | 5 | 27 | — |
| metsulfuron-methyl | 5 | 27 | — |
| chlorsulfuron | 5 | 34 | — |
| nicosulfuron | 5 | 11 | — |
| clethodim + thifensulfuron-methyl | 50 + 5 | 84.5 | 22 |
| clethodim + tribenuron-methyl | 50 + 5 | 83.2 | 17 |
| clethodim + cyclosulfamuron | 50 + 5 | 89.2 | 26 |
| clethodim + bensulfuron-methyl | 50 + 5 | 88.7 | 32 |
| clethodim + triasulfuron | 50 + 5 | 85.1 | 28 |
| clethodim + mesosulfuron-methyl | 50 + 5 | 34.2 | 5 |
| clethodim + monosulfuron | 50 + 5 | 86.7 | 24 |
| clethodim + amidosulfuron | 50 + 5 | 83.3 | 27 |
| clethodim + metsulfuron-methyl | 50 + 5 | 87.6 | 27 |
| clethodim + chlorsulfuron | 50 + 5 | 87.1 | 34 |
| clethodim + nicosulfuron | 50 + 5 | 57.2 | 11 |

TABLE 2

Herbicidal activity on *Setaria* four weeks after the treatment

| Treatment | Dosage Application rate in gram ai/ha | Injury of *Setaria* % Experimental value | Predicted value |
|---|---|---|---|
| clethodim | 50 | 57.4 | — |
| thifensulfuron-methyl | 1 | 0 | — |
| tribenuron-methyl | 1 | 0 | — |
| cyclosulfamuron | 1 | 0 | — |
| bensulfuron-methyl | 1 | 0 | — |
| triasulfuron | 1 | 0 | — |
| mesosulfuron-methyl | 1 | 0 | — |
| monosulfuron | 1 | 0 | — |
| amidosulfuron | 1 | 0 | — |
| metsulfuron-methyl | 1 | 0 | — |
| chlorsulfuron | 1 | 0 | — |
| nicosulfuron | 1 | 2 | — |
| clethodim + thifensulfuron-methyl | 50 + 1 | 78.2 | 57.4 |
| clethodim + tribenuron-methyl | 50 + 1 | 81.3 | 57.4 |
| clethodim + cyclosulfamuron | 50 + 1 | 79.3 | 57.4 |
| clethodim + bensulfuron-methyl | 50 + 1 | 73.2 | 57.4 |
| clethodim + triasulfuron | 50 + 1 | 76.5 | 57.4 |
| clethodim + mesosulfuron-methyl | 50 + 1 | 74.1 | 57.4 |
| clethodim + monosulfuron | 50 + 1 | 69.3 | 57.4 |
| clethodim + amidosulfuron | 50 + 1 | 70.5 | 57.4 |
| clethodim + metsulfuron-methyl | 50 + 1 | 71.4 | 57.4 |
| clethodim + chlorsulfuron | 50 + 1 | 74.1 | 57.4 |
| clethodim + nicosulfuron | 50 + 1 | 88.2 | 58.2 |

TABLE 3

Herbicidal activity on *Galium* four weeks after the treatment

| Treatment | Dosage Application rate in gram ai/ha | Injury of *Galium* % Experimental value | Predicted value |
|---|---|---|---|
| clethodim | 10 | 0 | — |
| thifensulfuron-methyl | 0.1 | 8 | — |
| tribenuron-methyl | 0.1 | 5 | — |
| cyclosulfamuron | 0.1 | 9 | — |
| bensulfuron-methyl | 0.1 | 16 | — |
| triasulfuron | 0.1 | 13 | — |
| mesosulfuron-methyl | 0.1 | 0 | — |
| monosulfuron | 0.1 | 7 | — |
| amidosulfuron | 0.1 | 5 | — |
| metsulfuron-methyl | 0.1 | 11 | — |
| chlorsulfuron | 0.1 | 10 | — |
| nicosulfuron | 0.1 | 1 | — |
| clethodim + thifensulfuron-methyl | 10 + 0.1 | 35.4 | 8 |
| clethodim + tribenuron-methyl | 10 + 0.1 | 30.1 | 5 |
| clethodim + cyclosulfamuron | 10 + 0.1 | 36.1 | 9 |
| clethodim + bensulfuron-methyl | 10 + 0.1 | 39.4 | 16 |
| clethodim + triasulfuron | 10 + 0.1 | 37.1 | 13 |
| clethodim + mesosulfuron-methyl | 10 + 0.1 | 18.2 | 0 |
| clethodim + monosulfuron | 10 + 0.1 | 23.5 | 7 |
| clethodim + amidosulfuron | 10 + 0.1 | 27.9 | 5 |
| clethodim + metsulfuron-methyl | 10 + 0.1 | 32.4 | 11 |
| clethodim + chlorsulfuron | 10 + 0.1 | 34.6 | 10 |
| clethodim + nicosulfuron | 10 + 0.1 | 35.3 | 1 |

TABLE 4

Herbicidal activity on *Alopecurus* four weeks after the treatment

| Treatment | Dosage Application rate in gram ai/ha | Injury of *Alopecurus* % Experimental value | Predicted value |
|---|---|---|---|
| clethodim | 1 | 5 | — |
| thifensulfuron-methyl | 10 | 0 | — |
| tribenuron-methyl | 10 | 0 | — |
| cyclosulfamuron | 10 | 0 | — |
| bensulfuron-methyl | 10 | 0 | — |
| triasulfuron | 10 | 0 | — |
| mesosulfuron-methyl | 10 | 75 | — |
| monosulfuron | 10 | 5 | — |
| amidosulfuron | 10 | 0 | — |
| metsulfuron-methyl | 10 | 82 | — |
| chlorsulfuron | 10 | 54 | — |
| nicosulfuron | 10 | 5 | — |
| clethodim + thifensulfuron-methyl | 1 + 10 | 34.4 | 5 |
| clethodim + tribenuron-methyl | 1 + 10 | 28.2 | 5 |
| clethodim + cyclosulfamuron | 1 + 10 | 17.4 | 5 |
| clethodim + bensulfuron-methyl | 1 + 10 | 19.5 | 5 |
| clethodim + triasulfuron | 1 + 10 | 21.4 | 5 |
| clethodim + mesosulfuron-methyl | 1 + 10 | 93.3 | 76.25 |
| clethodim + monosulfuron | 1 + 10 | 27.3 | 9.75 |
| clethodim + amidosulfuron | 1 + 10 | 19.2 | 5 |
| clethodim + metsulfuron-methyl | 1 + 10 | 90.6 | 82.9 |
| clethodim + chlorsulfuron | 1 + 10 | 78.4 | 56.3 |
| clethodim + nicosulfuron | 1 + 10 | 28.3 | 9.75 |

TABLE 5

Herbicidal activity on *Stellaria* four weeks after the treatment

| Treatment | Dosage Application rate in gram ai/ha | Injury of *Stellaria* % Experimental value | Predicted value |
|---|---|---|---|
| clethodim | 10 | 0 | — |
| thifensulfuron-methyl | 10 | 57 | — |
| tribenuron-methyl | 10 | 36 | — |
| cyclosulfamuron | 10 | 48 | — |
| bensulfuron-methyl | 10 | 64 | — |
| triasulfuron | 10 | 40 | — |
| mesosulfuron-methyl | 10 | 72 | — |
| monosulfuron | 10 | 34 | — |
| amidosulfuron | 10 | 35 | — |
| metsulfuron-methyl | 10 | 58 | — |
| chlorsulfuron | 10 | 55 | — |
| nicosulfuron | 10 | 60 | — |
| clethodim + thifensulfuron-methyl | 10 + 10 | 91.3 | 57 |
| clethodim + tribenuron-methyl | 10 + 10 | 84.6 | 36 |
| clethodim + cyclosulfamuron | 10 + 10 | 89.3 | 48 |
| clethodim + bensulfuron-methyl | 10 + 10 | 94.5 | 64 |
| clethodim + triasulfuron | 10 + 10 | 85.1 | 40 |
| clethodim + mesosulfuron-methyl | 10 + 10 | 87.3 | 72 |
| clethodim + monosulfuron | 10 + 10 | 80.1 | 34 |
| clethodim + amidosulfuron | 10 + 10 | 81.2 | 35 |
| clethodim + metsulfuron-methyl | 10 + 10 | 92.7 | 58 |
| clethodim + chlorsulfuron | 10 + 10 | 88.4 | 55 |
| clethodim + nicosulfuron | 10 + 10 | 93.9 | 60 |

TABLE 6

Herbicidal activity on *Chenopodium* four weeks after the treatment

| Treatment | Dosage Application rate in gram ai/ha | Injury of *Chenopodium* % Experimental value | Predicted value |
|---|---|---|---|
| sethoxydim | 0.1 | 0 | — |
| thifensulfuron-methyl | 10 | 8.1 | — |
| tribenuron-methyl | 10 | 24.2 | — |
| cyclosulfamuron | 10 | 4.1 | — |
| bensulfuron-methyl | 10 | 12.2 | — |
| triasulfuron | 10 | 22.5 | — |
| mesosulfuron-methyl | 10 | 11.1 | — |
| monosulfuron | 10 | 23.5 | — |
| amidosulfuron | 10 | 35.8 | — |
| metsulfuron-methyl | 10 | 88.4 | — |
| chlorsulfuron | 10 | 53.6 | — |
| nicosulfuron | 10 | 4 | — |
| sethoxydim + thifensulfuron-methyl | 0.1 + 10 | 22.6 | 8.1 |
| sethoxydim + tribenuron-methyl | 0.1 + 10 | 45.7 | 24.2 |
| sethoxydim + cyclosulfamuron | 0.1 + 10 | 18.9 | 4.1 |
| sethoxydim + bensulfuron-methyl | 0.1 + 10 | 32.8 | 12.2 |
| sethoxydim + triasulfuron | 0.1 + 10 | 38.5 | 22.5 |
| sethoxydim + mesosulfuron-methyl | 0.1 + 10 | 24.7 | 11.1 |
| sethoxydim + monosulfuron | 0.1 + 10 | 42.1 | 23.5 |
| sethoxydim + amidosulfuron | 0.1 + 10 | 48.7 | 35.8 |
| sethoxydim + metsulfuron-methyl | 0.1 + 10 | 100 | 88.4 |
| sethoxydim + chlorsulfuron | 0.1 + 10 | 76.4 | 53.6 |
| sethoxydim + nicosulfuron | 0.1 + 10 | 12.6 | 4 |

TABLE 7

Herbicidal activity on *Beckmannia* four weeks after the treatment

| Treatment | Dosage Application rate in gram ai/ha | Injury of *Beckmannia* % Experimental value | Predicted value |
|---|---|---|---|
| sethoxydim | 0.2 | 0 | — |
| thifensulfuron-methyl | 10 | 0 | — |
| tribenuron-methyl | 10 | 0 | — |
| cyclosulfamuron | 10 | 0 | — |
| bensulfuron-methyl | 10 | 0 | — |
| triasulfuron | 10 | 0 | — |
| mesosulfuron-methyl | 10 | 76 | — |
| monosulfuron | 10 | 7 | — |
| amidosulfuron | 10 | 0 | — |
| metsulfuron-methyl | 10 | 24.8 | — |
| chlorsulfuron | 10 | 36.2 | — |
| nicosulfuron | 10 | 50.3 | — |
| sethoxydim + thifensulfuron-methyl | 0.2 + 10 | 18.4 | 0 |
| sethoxydim + tribenuron-methyl | 0.2 + 10 | 22.1 | 0 |
| sethoxydim + cyclosulfamuron | 0.2 + 10 | 15.2 | 0 |
| sethoxydim + bensulfuron-methyl | 0.2 + 10 | 18.2 | 0 |
| sethoxydim + triasulfuron | 0.2 + 10 | 11.8 | 0 |
| sethoxydim + mesosulfuron-methyl | 0.2 + 10 | 89.6 | 76 |
| sethoxydim + monosulfuron | 0.2 + 10 | 38.6 | 7 |
| sethoxydim + amidosulfuron | 0.2 + 10 | 16.7 | 0 |
| sethoxydim + metsulfuron-methyl | 0.2 + 10 | 59.2 | 24.8 |
| sethoxydim + chlorsulfuron | 0.2 + 10 | 61.6 | 36.2 |
| sethoxydim + nicosulfuron | 0.2 + 10 | 68.7 | 50.3 |

The invention has been described with respect to certain specific embodiments thereof, but those skilled in the art will recognize that these specific embodiments are exemplary, rather than limiting, of the appended claims.

The invention claimed is:

1. A synergistically effective amount of a synergistic herbicidal composition, comprising a combination of a compound A and a compound B; wherein the compound A is at least one selected from the group consisting of clethodim and sethoxydim; and wherein the compound B is at least one selected from the group consisting of thifensulfuron-methyl, tribenuron-methyl, cyclosulfamuron, bensulfuron-methyl, triasulfuron, mesosulfuron-methyl, monosulfuron, amidosulfuron, metsulfuron-methyl, chlorsulfuron and nicosulfuron; and wherein the weight ratio between the compound A and the compound B is in the range from 100:1 to 1:100.

2. The synergistic herbicidal composition according to claim 1, wherein the weight ratio between the compound A and the compound B is in the range from 50:1 to 1:50.

3. The synergistic herbicidal composition according to claim 1, wherein the weight ratio between the compound A and the compound B is in the range from 10:1 to 1:10.

4. The synergistic herbicidal composition according to claim 1, wherein the combination of the compound (A) and the compound (B) of the composition are:
   (1) clethodim+thifensulfuron-methyl;
   (2) clethodim+tribenuron-methyl;
   (3) clethodim+cyclosulfamuron;
   (4) clethodim+bensulfuron-methyl;
   (5) clethodim+triasulfuron;
   (6) clethodim+mesosulfuron-methyl;
   (7) clethodim+monosulfuron;
   (8) clethodim+amidosulfuron;
   (9) clethodim+metsulfuron-methyl;
   (10) clethodim+chlorsulfuron;
   (11) clethodim+nicosulfuron;
   (12) sethoxydim+thifensulfuron-methyl;
   (13) sethoxydim+tribenuron-methyl;
   (14) sethoxydim+cyclosulfamuron;
   (15) sethoxydim+bensulfuron-methyl;
   (16) sethoxydim+triasulfuron;
   (17) sethoxydim+mesosulfuron-methyl;
   (18) sethoxydim+monosulfuron;
   (19) sethoxydim+amidosulfuron;
   (20) sethoxydim+metsulfuron-methyl;
   (21) sethoxydim+chlorsulfuron; or
   (22) sethoxydim+nicosulfuron.

5. The synergistic herbicidal composition according to claim 1, wherein the synergistic herbicidal composition is an agriculturally acceptable formulation.

6. The synergistic herbicidal composition according to claim 5, wherein the agriculturally acceptable formulation is selected from the group consisting of wettable powders, emulsifiable concentrates, suspension concentrates, oil-based suspension concentrates, micro-capsules, micro-emulsions, oil-in-water emulsion, suspo-emulsions, water dispersible granules, a mixed formulation of microencapsulated suspension and suspension concentrate (ZC) and ultra-low volume liquids.

7. A method of producing the synergistic herbicidal composition according to claim 1, comprising mixing a combination containing the compound (A) and the compound (B) with at least one agriculturally acceptable additive.

8. A method for controlling undesired plants, comprising applying the synergistic herbicidal composition according to claim 1 to a plant, plant tissue, plant seed, or cultivation area during preemergence or during postemergence, or during preemergence and postemergence.

9. A method for controlling the growth of undesired plants in fields of resistant rape crops, or resistant soybean crops, or both, comprising applying the synergistic herbicidal composition according to claim 1 to undesired plants, plant tissues thereof, or cultivation areas.

10. The method according to claim 8, wherein the undesired plants are monocotyledonous weeds, dicotyledonous weeds, or a combination thereof.

* * * * *